United States Patent
Ejiri et al.

(10) Patent No.: US 10,602,952 B2
(45) Date of Patent: Mar. 31, 2020

(54) APPARATUS FOR GUIDING BIOMEDICAL ELECTRODE

(71) Applicant: SMK Corporation, Tokyo (JP)

(72) Inventors: Koichiro Ejiri, Kanagawa (JP); Haruhiko Kondo, Kanagawa (JP)

(73) Assignee: SMK Corporation, Tokyo (JP)

( * ) Notice: Subject to any disclaimer, the term of this patent is extended or adjusted under 35 U.S.C. 154(b) by 298 days.

(21) Appl. No.: 15/702,711

(22) Filed: Sep. 12, 2017

(65) Prior Publication Data

US 2018/0249923 A1    Sep. 6, 2018

(30) Foreign Application Priority Data

Mar. 2, 2017 (JP) .................................. 2017-39545

(51) Int. Cl.
*A61B 5/0492* (2006.01)
*A61B 5/00* (2006.01)
(Continued)

(52) U.S. Cl.
CPC .......... *A61B 5/0492* (2013.01); *A61B 5/0035* (2013.01); *A61B 5/4887* (2013.01); *A61B 5/4893* (2013.01); *A61B 5/742* (2013.01); *A61B 5/7405* (2013.01); *A61B 5/04001* (2013.01); *A61B 5/0488* (2013.01); *A61B 5/45* (2013.01); *A61B 5/7425* (2013.01); *A61B 2562/046* (2013.01); *A61N 1/0476* (2013.01); *G16H 30/40* (2018.01)

(58) Field of Classification Search
CPC .... A61N 1/0476; G16H 30/40; A61B 5/0488; A61B 5/04001; A61B 5/7425; A61B 5/04; A61B 5/45; A61B 5/742
See application file for complete search history.

(56) References Cited

U.S. PATENT DOCUMENTS

2005/0288586 A1*  12/2005  Ferek-Petric ........ A61B 8/0833
                                                               600/443
2006/0129057 A1*  6/2006  Maekawa ............. A61B 5/0488
                                                              600/546
(Continued)

OTHER PUBLICATIONS

Ken Nishihara et al., Estimation of muscle fiber conduction velocity by pulse detection averaging method and analysis of muscle fatigue,Senmon rehabil,2003, pp. 42-47, vol. 2,Senmon Rehabilitation Research Society, Japan.

*Primary Examiner* — Christian Jang
*Assistant Examiner* — Karen E Toth (57) ABSTRACT

An apparatus for guiding a biomedical electrode is provided, which guides a biomedical electrode to be brought into close contact with a living body surface of a voluntary muscle into optimum close contact positions on the basis of positions of the voluntary muscle and a neuromuscular junction of the voluntary muscle inside the living body surface. The relative positions of the voluntary muscle and the neuromuscular junction of the voluntary muscle to the living body surface are detected from muscle action potentials detected by myoelectric detection electrodes put into close contact with a large number of positions on the living body surface. On the basis of the relative position information, a close contact position of the biomedical electrode to be brought into close contact with the living body surface of the voluntary muscle is guided to an optimum position.

5 Claims, 8 Drawing Sheets

(51) Int. Cl.
*A61N 1/04* (2006.01)
*A61B 5/0488* (2006.01)
*G16H 30/40* (2018.01)
*A61B 5/04* (2006.01)

(56) References Cited

U.S. PATENT DOCUMENTS

| | | | |
|---|---|---|---|
| 2007/0074728 A1* | 4/2007 | Rea | A61B 5/04886 128/207.14 |
| 2008/0077041 A1* | 3/2008 | Gozani | A61B 5/05 600/547 |
| 2017/0188880 A1* | 7/2017 | Sela | A61B 5/06 |
| 2017/0197074 A1 | 7/2017 | Ono et al. | |

* cited by examiner

APPARATUS FOR GUIDING BIOMEDICAL ELECTRODE

CROSS REFERENCE TO RELATED APPLICATION

The contents of the following Japanese patent application are incorporated herein by reference,
Japanese Patent Application No. 2017-39545 filed on Mar. 2, 2017.

FIELD

The present invention relates to an apparatus for guiding a biomedical electrode for bringing a biomedical electrode into close contact with a body surface of a muscle for the purpose of detecting an action potential of the muscle from the biomedical electrode in close contact with the body surface of the muscle to detect a state of the muscle inside the body surface.

BACKGROUND

Figure 5:
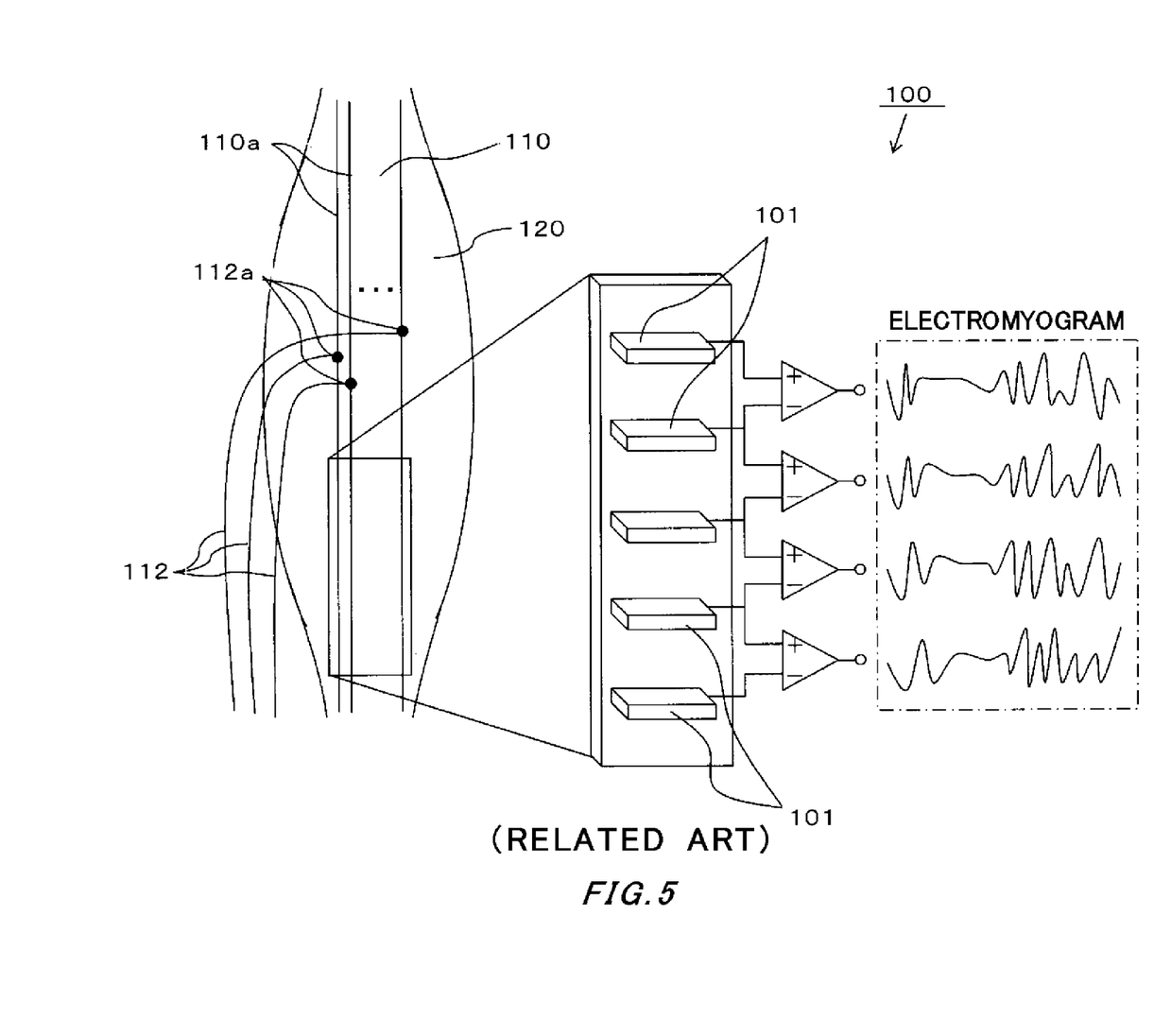
FIG. 5 is a schematic diagram showing a related evaluation apparatus 100 which detects muscle action potentials from a plurality of respective myoelectric detection electrodes 101 put in close contact with the body surface 120 of the muscle 110.

When a voluntary muscle makes a voluntary movement, a muscle action potential occurs in the muscle. There is known an evaluation system which evaluates a composition and an activity status, such as fatigue, of a muscle on the basis of the position of a body surface where a muscle action potential is detected, and propagation velocity and the like of the muscle action potential. FIG. 5 shows a related evaluation apparatus 100. A plurality of myoelectric detection electrodes 101 are brought into close contact with a body surface 120 of a muscle 110, and muscle action potentials are detected from the respective myoelectric detection electrodes 101. A degree of fatigue of the muscle is evaluated from propagation velocity (muscle fiber conduction velocity: MFCV) of the muscle action potentials along muscle fibers 110a (Non-Patent Literature 1).

As shown in FIG. 5, a motor command from the central nervous system initially propagates as electric excitation to neuromuscular junctions 112a through motor axons 112. Acetylcholine emitted from the nerve endings acts on the end-plates on the muscle fiber side of the neuromuscular junctions 112a. Muscle action potentials occur thus at the end-plates when the voluntary muscle contracts. In general, the neuromuscular junctions (end-plates) 112a lie in the center of the muscle fibers 110a. The muscle action potentials occurring in the neuromuscular junctions 112a propagate from the center of the muscle fibers 110a to both sides in a longitudinal direction of the muscle 110 along the muscle fibers 110a. In the evaluation apparatus 100, myoelectric detection electrodes 101 are put in close contact with a plurality of positions on the body surface 120 along the direction of the muscle fibers 110a from the neuromuscular junctions 112a to a peripheral side. A difference between muscle action potentials detected from a pair of myoelectric detection electrodes 101, 101 adjoining in the direction of arrangement will be referred to as a muscle action potential detected by the pair of myoelectric detection electrodes. Muscle action potentials detected by respective pairs are plotted on an electromyogram with the horizontal axis as a time axis. The propagation velocity MFCV of the muscle action potentials is determined from the electromyogram.

For the purpose of rehabilitation, there is known a rehabilitation support system which applies an electrical stimulation signal to a muscle to expand and contract the muscle for training. A plurality of biomedical electrodes are brought into close contact with the body surface of the muscle to be trained, and an electrical stimulation signal is applied to the muscle inside the body surface via the biomedical electrodes to forcefully expand and contract the muscle. To evaluate the efficiency and effect of training of the muscle by the electrical stimulus, a relationship between the position of the electrical stimulus and the patient's reaction caused by the electrical stimulus is recorded upon each training session, and an evaluation is made on the basis of the transition of the relationship. For accurate comparison of changes in reaction, the biomedical electrodes need to be put in close contact with the same positions on the body surface in each training session. Patent Literature 1 describes a rehabilitation support system which obtains positions where biomedical electrodes are put in close contact with a body surface from a triangular shape of the body's outline, marks attached to the body, an auxiliary scale, feature points on the body, etc. The rehabilitation support system displays the close contact positions of the biomedical electrodes along with an image showing the body surface, so that the biomedical electrodes are guided into close contact with the same positions on the body surface in the next training session of the muscle.

CITATION LIST

Patent Literature

Patent Literature 1: Japanese Patent Application Laid-Open No. 2015-228958
Non-Patent Literature 1: Nishihara, Ken, et al., Japanese journal of allied health and rehabilitation, 2003, Senmon rehabil, vol. 2, p. 43

SUMMARY

Technical Problem

The evaluation apparatus 100 detects muscle action potentials occurring in the muscle 110 from the myoelectric detection electrodes 101 in close contact with the body surface 120 of the muscle 110. If the myoelectric detection electrodes 101 are in close contact with a position of the body surface 120 off the muscle 110 to be evaluated, the detection levels of the muscle action potentials decrease and an accurate electromyogram fails to be created. The myoelectric detection electrodes 101 therefore have been brought into close contact with the position of the body surface 120 of the muscle 110 to be evaluated, according to the position of the muscle 110 inside the body surface of the body based on an anatomical observation. However, the position, size, and shape of the muscle 110 vary between individuals. Even for the same person, the shape varies depending on the state of expansion and contraction of the muscle 110. The myoelectric detection electrodes 101 are therefore unable to be accurately brought into close contact with the body surface 120 where the muscle 110 lies.

Even if an approximate position of the muscle 110 under the body surface can be found out, the position of the neuromuscular junction 112a at which the muscle action potential occurs first and the direction of the muscle fibers 110 are unable to be accurately figured out. Therefore, even if the myoelectric detection electrodes 101 are put in close contact with the body surface 120 of the muscle 110, the muscle action potential and the propagation velocity MFCV of the muscle action potential may fail to be detected.

Figure 6A:
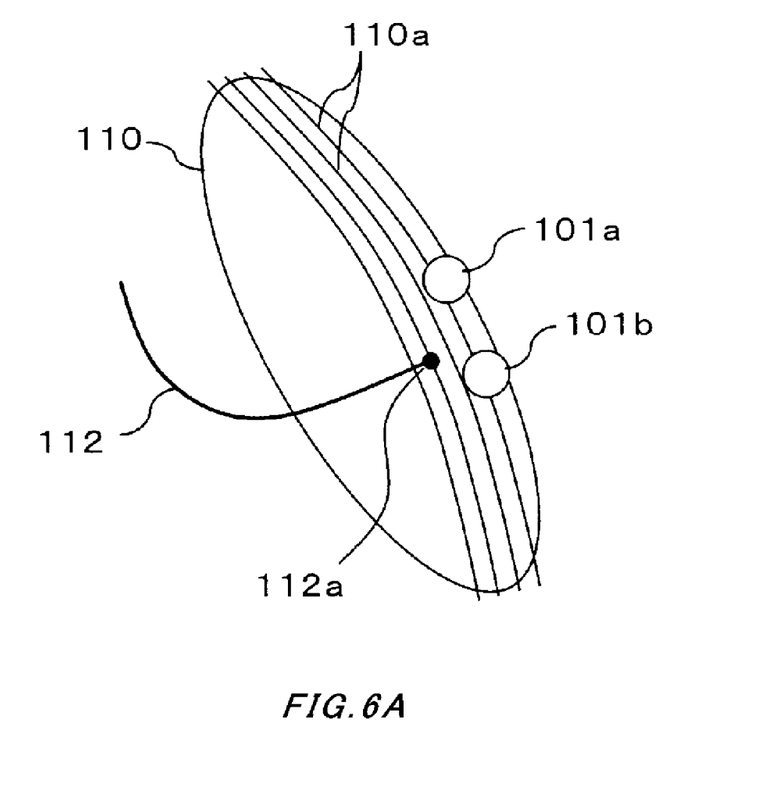
FIG. 6A is an explanatory diagram showing a state in which a pair of adjoining myoelectric detection electrodes 101a and 101b are in close contact with positions on both sides of a body surface 120 with a neuromuscular junction 112a interposed therebetween.

For example, suppose, as shown in FIG. 6A, that a pair of adjoining myoelectric detection electrodes 101a and 101b are in close contact with positions on both sides of the body surface 120 with a neuromuscular junction 112a interposed therebetween. In such a case, the muscle action potential detected from a difference between the muscle action potentials occurring at the pair of myoelectric detection electrodes 101a and 101b reverses in polarity depending on which of the myoelectric detection electrodes 101a and 101b is closer to the neuromuscular junction 112a. The muscle action potential becomes zero if the two electrodes are at equal distances. The result is that an accurate muscle action potential is unable to be detected from the pair of myoelectric detection electrodes 101a and 101b.

Figure 6B:
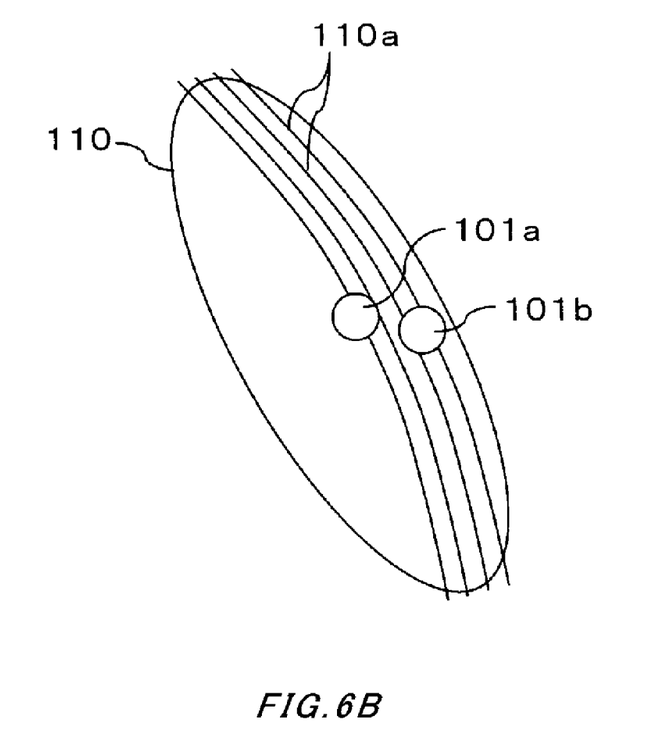

Suppose, as shown in FIG. 6B, that the pair of adjoining myoelectric detection electrodes 101a and 101b are not in close contact with positions on the body surface 120 along the longitudinal direction of the voluntary muscle 110 which is the running direction of the muscle fibers 110a. In such a case, the myoelectric detection electrodes 101a and 101b detect muscle action potentials propagating through different muscle fibers 110a. The detection time at which a muscle action potential is detected by the pair of myoelectric detection electrodes 101a and 101b is therefore not accurate. This causes an error in the propagation velocity MFCV of the muscle action potential calculated from a difference between the detection times of respective two or more pairs of myoelectric detection electrodes 101a and 101b.

The rehabilitation system described in Patent Literature 1 includes guiding means for guiding muscle stimulating electrodes to the same positions on the body surface as in the previous training session. However, since the accurate position of the muscle or the accurate longitudinal direction of the muscle is not known, the muscle stimulating electrodes are unable to be brought into close contact with stimulation positions on the body surface where the training effect is highest.

Solution to Problem

The present invention has been achieved in view of the foregoing conventional problems. An object of the present invention is to provide an apparatus for guiding a biomedical electrode for accurately guiding a close contact position of a biomedical electrode to be brought into close contact with a living body surface of a voluntary muscle on the basis of relative positions of the voluntary muscle and a neuromuscular junction of the voluntary muscle to the living body surface.

Another object of the present invention is to provide an apparatus for guiding a biomedical electrode, by which a plurality of biomedical electrodes can be brought into close contact with a body surface along the direction of muscle fibers so that the propagation velocity MFCV of a muscle action potential can be accurately detected.

To achieve the foregoing object, an apparatus for guiding a biomedical electrode according to a first aspect of the present invention includes: a plurality of myoelectric detection electrodes that make close contact with respective positions on a living body surface and each detect a muscle action potential occurring when a voluntary muscle inside the living body surface expands and contracts, the positions being distributed over a two-dimensional plane; a muscle position detecting unit for detecting a relative position of the voluntary muscle and/or a neuromuscular junction of the voluntary muscle to the living body surface from a myoelectric potential distribution of the muscle action potentials detected by the respective myoelectric detection electrodes over the two-dimensional plane and/or a temporal change of the myoelectric potential distribution; a storing unit for storing relative position information about the voluntary muscle and/or the neuromuscular junction of the voluntary muscle to the living body surface; and a guiding unit for guiding a close contact position of a biomedical electrode to be brought into close contact with the living body surface of the voluntary muscle on the basis of the relative position information.

The plurality of myoelectric detection electrodes make close contact with the respective positions on the living body surface, which are distributed over the two-dimensional plane. The muscle position detecting unit can thus detect the relative position(s) of the voluntary muscle and/or the neuromuscular junction of the voluntary muscle under the living body surface relative to the living body surface from the myoelectric potential distribution of the muscle action potentials detected by the respective myoelectric potential detection electrodes over the two-dimensional plane and/or the temporal change of the myoelectric potential distribution. The guiding unit guides the close contact position of the biomedical electrode on the basis of the relative position information about the voluntary muscle and/or the neuromuscular junction of the voluntary muscle. The biomedical electrode can thus be brought into close contact with a position where the muscle action potential and the propagation velocity of the muscle action potential can be accurately detected.

In the apparatus for guiding a biomedical electrode according to a second aspect, the relative position information is a muscle position display map image in which the voluntary muscle and/or the neuromuscular junction of the voluntary muscle of which the relative position(s) is/are detected by the muscle position detecting unit is/are superposed and displayed on an image showing the living body surface.

The muscle position display map image displays the voluntary muscle and/or the neuromuscular junction of the voluntary muscle under the living body surface, on the image showing the living body surface.

In the apparatus for guiding a biomedical electrode according to a third aspect, the guiding unit includes: a camera that captures a moving image of a state in which the biomedical electrode is brought close to the living body surface of the voluntary muscle; an image composition unit for combining the muscle position display map image with the moving image to generate a composite moving image so that feature portion images of the living body surface included in the muscle position display map image and the moving image in common coincide; and a display device that displays the composite moving image.

The composite moving image displays the biomedical electrode to be brought into close contact with respect to the living body surface in a superposed manner on the muscle position display map image which displays the position(s) of the voluntary muscle and/or the neuromuscular junction of the voluntary muscle under the living body surface.

In the apparatus for guiding a biomedical electrode according to a fourth aspect, the guiding unit displays a marker indicating the voluntary muscle and/or the neuromuscular junction of the voluntary muscle on the living body surface of the voluntary muscle for the biomedical electrode to be brought close to on the basis of the relative position information.

The marker indicating the position(s) of the voluntary muscle and/or the neuromuscular junction of the voluntary muscle under the living body surface is displayed on the living body surface.

In the apparatus for guiding a biomedical electrode according to a fifth aspect, the guiding unit expresses, by sound or display, a distance between the voluntary muscle and/or the neuromuscular junction of the voluntary muscle and the biomedical electrode to be brought close to the living body surface of the voluntary muscle on the basis of the relative position information.

The distance between the voluntary muscle and/or the neuromuscular junction of the voluntary muscle and the biomedical electrode to be brought close to the living body surface is conveyed to the user by sound or display.

In the apparatus for guiding a biomedical electrode according to a sixth aspect, the muscle position detecting unit detects the relative position of the voluntary muscle to the living body surface. The guiding unit guides at least a pair of biomedical electrodes to different close contact positions on the living body surface along a longitudinal direction of the voluntary muscle, the biomedical electrodes each detecting a muscle action potential occurring from the voluntary muscle.

The pair of biomedical electrodes guided to the different close contact positions on the living body surface along the longitudinal direction of the voluntary muscle detect a muscle action potential propagating along the same muscle fiber.

In the apparatus for guiding a biomedical electrode according to a seventh aspect, the muscle position detecting unit detects the relative positions of the voluntary muscle and the neuromuscular junction of the voluntary muscle to the living body surface. The guiding unit guides at least a pair of biomedical electrodes to close contact positions on the living body surface on one side of the neuromuscular junction of the voluntary muscle in the longitudinal direction of the voluntary muscle.

The pair of biomedical electrodes are guided to different close contact positions on the living body surface along the longitudinal direction of the voluntary muscle, on one side of the voluntary muscle with respect to the neuromuscular junction of the voluntary muscle. The pair of biomedical electrodes detect a muscle action potential propagating from the neuromuscular junction of the voluntary muscle in the same direction along the direction of muscle fibers. A muscle action potential detected from a difference appearing between the pair of biomedical electrodes is obtained from a difference between the muscular action potential appearing at one of the pair of the biomedical electrodes closer to the neuromuscular junction and the muscular action potential appearing at one farther from the neuromuscular junction. An accurate muscle action potential is thus always detected from the pair of biomedical electrodes.

According to the invention of the first aspect, the relative position information indicating the relative position(s) of the voluntary muscle and/or the neuromuscular junction of the voluntary muscle under the living body surface to the living body surface is used to guide the close contact position of the biomedical electrode to be brought into close contact with the living body surface of the voluntary muscle. The biomedical electrode can thus be brought into close contact with a position where the muscle action potential and the propagation velocity MFCV of the muscle action potential can be accurately detected.

The biomedical electrode may be a stimulating electrode for applying an electrical stimulation signal. On the basis of the relative position information indicating the relative position(s) of the voluntary muscle and/or the neuromuscular junction of the voluntary muscle under the living body surface, the stimulating electrode can be brought into close contact with a position on the living body surface where an electrical stimulus can be most effectively applied to the muscle.

According to the invention of the second aspect, the position(s) of the voluntary muscle and/or the neuromuscular junction of the voluntary muscle under the living body surface can be visually checked. The biomedical electrode can thus be easily brought into close contact with an optimum position on the body surface of the muscle.

According to the invention of the third aspect, the close contact position of the living electrode can be checked while viewing the composite moving image in which the voluntary muscle and/or the neuromuscular junction of the voluntary muscle under the living body surface and the biomedical electrode to be brought into close contact are displayed with respect to the living body surface.

According to the invention of the fourth aspect, the marker indicating the position(s) of the voluntary muscle and/or the neuromuscular junction of the voluntary muscle under the living body surface is displayed on the living body surface. The biomedical electrode can thus be easily brought into close contact with an optimum position on the body surface of the muscle.

According to the invention of the fifth aspect, the distance between the voluntary muscle and/or the neuromuscular junction of the voluntary muscle and the biomedical electrode to be brought close to the living body surface is conveyed to the user by sound or display. The biomedical electrode can thus be easily brought into close contact with an optimum position on the body surface of the muscle.

According to the invention of the sixth aspect, the pair of biomedical electrodes are guided to different contact positions on the living body surface along the longitudinal direction of the voluntary muscle, so that the pair of biomedical electrodes can detect the muscle action potential propagating along the same muscle fiber. The detection time of the muscle action potential detected by the pair of biomedical electrodes includes few errors. An accurate propagation velocity MFCV of the muscle action potential is thus obtained from a difference between the detection times of two or more pairs of biomedical electrodes.

According to the invention of the seventh aspect, the muscle action potential propagating from the neuromuscular junction along the muscle fiber appears in order, always from one of the pair of biomedical electrodes. The muscle action potential can thus be accurately detected from the pair of biomedical electrodes.

BRIEF DESCRIPTION OF DRAWINGS

FIG. 6B is an explanatory diagram showing a state in which the pair of adjoining myoelectric detection electrodes 101a and 101b are in close contact with positions on the body surface 120 across a running direction of muscle fibers 110a.

DESCRIPTION OF EMBODIMENTS

Figure 1:
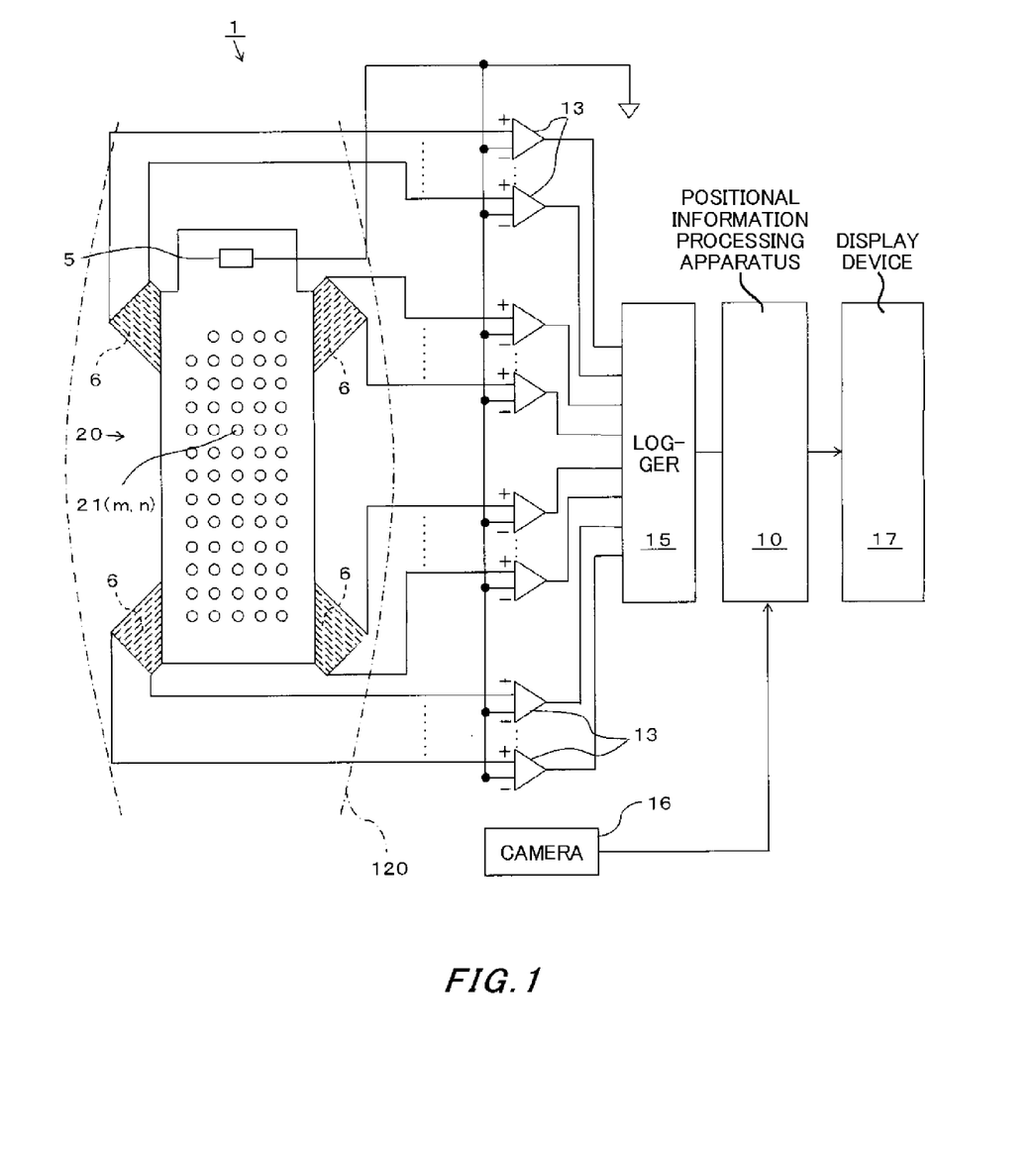
FIG. 1 is a block diagram of an apparatus 1 for guiding a biomedical electrode according to an embodiment of the present invention.

An apparatus 1 for guiding a biomedical electrode according to an embodiment of the present invention will be described with reference to FIGS. 1 to 4D. As shown in FIG. 1, the apparatus 1 for guiding a biomedical electrode includes an electrode sheet 20, 64 comparison circuits 13, 13, . . . , a logger 15, a camera 16, a positional information processing apparatus 10, and a display device 17. Sixty-four myoelectric detection electrodes 21(m, n) to be brought into close contact with a living body surface (body surface) 120 of a muscle 110 are attached to the electrode sheet 20. The 64 comparison circuits 13, 13, . . . each compare potentials appearing at the respective myoelectric detection electrodes 21(m, n) with a ground potential, and output the results as muscle action potentials to the logger 15. The logger 15 records the muscle action potentials output from the comparison circuits 13, 13, . . . with elapsed time. The camera 16 captures a still image and a moving image of the living body surface 120 of the muscle 110. The positional information processing apparatus 10 detects relative positions of the muscle 110 and a neuromuscular junction 112a of the muscle 110 to the living body surface 120 from the results recorded in the logger 15. On the basis of the relative position information, the positional information processing apparatus 10 generates a composite moving image by adding marks 31a indicating the position of the muscle 110 and a mark 31b indicating the position of the neuromuscular junction 112a to the moving image captured by the camera 16. The display device 17 displays the composite moving image generated by the positional information processing apparatus 10.

As shown in FIG. 1, the electrode sheet 20 includes a flexible printed wiring board made of a flexible insulating sheet of PET or the like. A ground electrode 5 set to a ground potential, the 64 myoelectric detection electrodes 21(m, n), and 64 lead traces 6 connected to the respective myoelectric detection electrodes 21(m, n) are formed on the bottom side of the insulating sheet by printing. The 64 myoelectric detection electrodes 21(m, n) are arranged in respective positions in a 13-row by 5-column matrix, except the first-row first-column position at the upper left corner of the bottom of the insulating sheet. The 64 lead traces 6 are laid from the respective myoelectric detection electrodes 21(m, n) to tail portions at the four corners of the insulating sheet. The 64 lead traces 6 are connected to noninverting inputs of the respective 64 comparison circuits 13, 13, . . . via connection cables. The lead traces 6 are covered with a resist at the side opposed to the body surface and thereby insulated from the body surface.

For example, suppose that the muscle 110 which to detect the relative position of and the relative position of the neuromuscular junction 112a of with respect to the living body surface 120 is a brachial muscle 110. The electrode sheet 20 is shaped to cover the living body surface 120 under which the brachial muscle 110 is estimated to be. An adhesive layer formed on the entire bottom surface of the electrode sheet 20, except portions in which the ground electrode 5 and the 64 myoelectric detection electrodes 21(m, n) are exposed, is adhered to the living body surface 120 where the brachial muscle 110 is.

With the adhesive layer of the electrode sheet 20 adhered to the living body surface 120, the 64 myoelectric detection electrodes 21(m, n) make close contact with respective different positions distributed over the living body surface 120 of the brachial muscle 110. Potentials appearing at the close contact positions are output to the noninverting inputs of the comparison circuits 13. The comparison circuits 13 output the potentials appearing at the respective myoelectric detection electrodes 21(m, n), compared with the ground potential, to the logger 15.

The logger 15 records the potentials detected by all the myoelectric detection electrodes 21(m, n), output from the comparison circuits 13, 13, . . . , and outputs the recorded potentials to the positional information processing apparatus 10 each time a certain time elapses.

Figure 2:
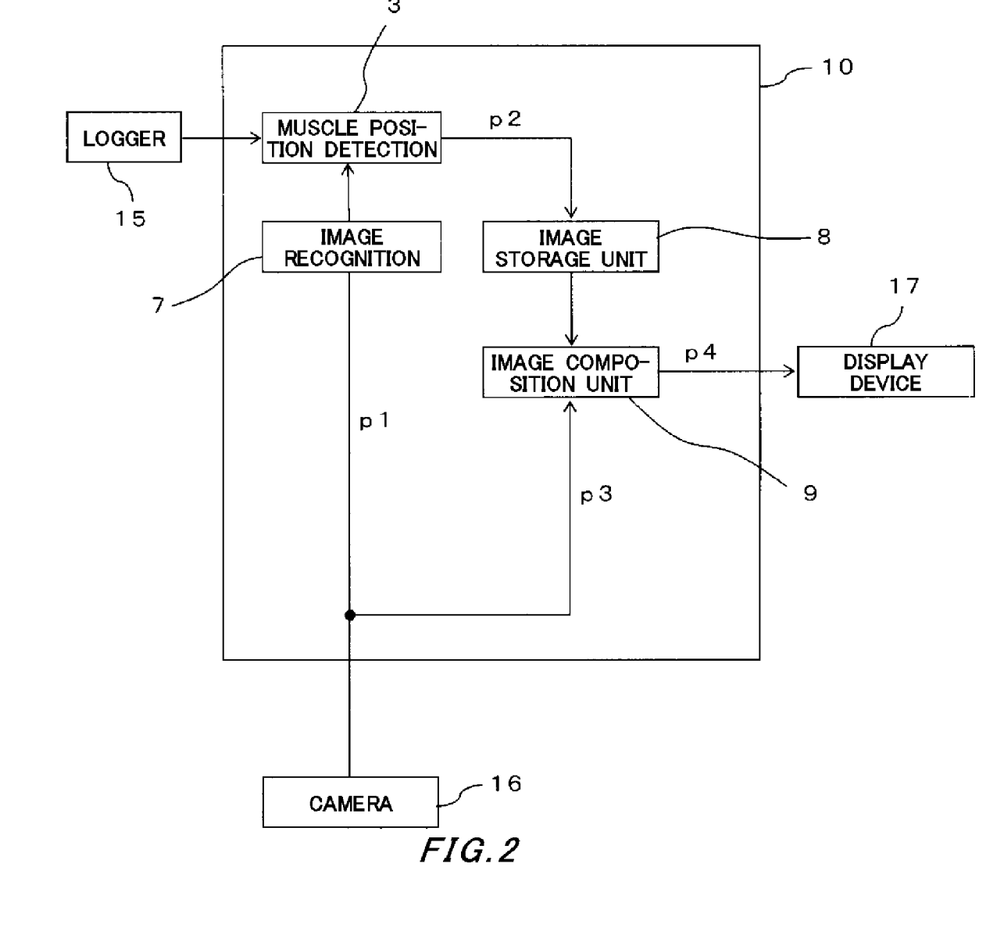
FIG. 2 is a block diagram of a positional information processing apparatus 10.
Figure 4A:
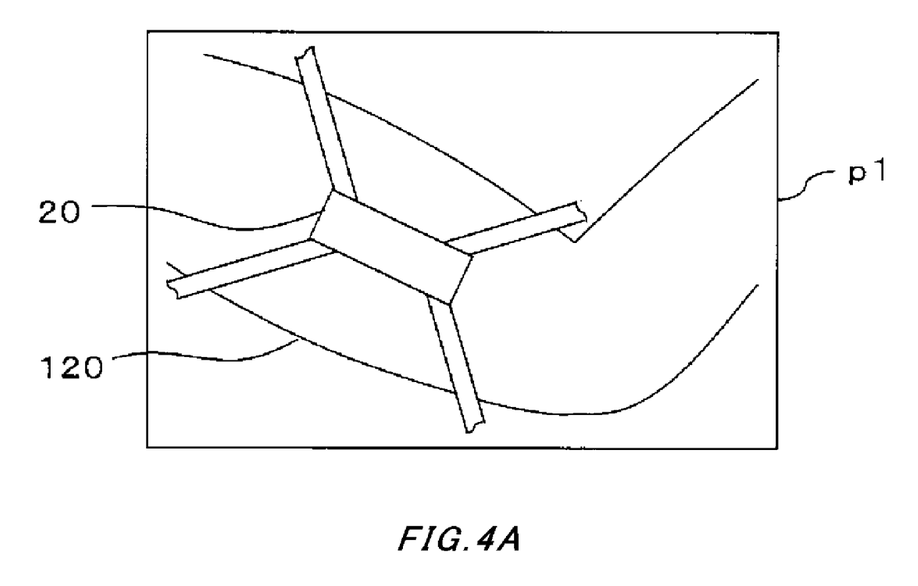
FIG. 4A is an explanatory diagram showing images processed by the positional information processing apparatus 10, showing a still image p1 of an electrode sheet 20 attached to a body surface 120 of a muscle 110.
Figure 4B:
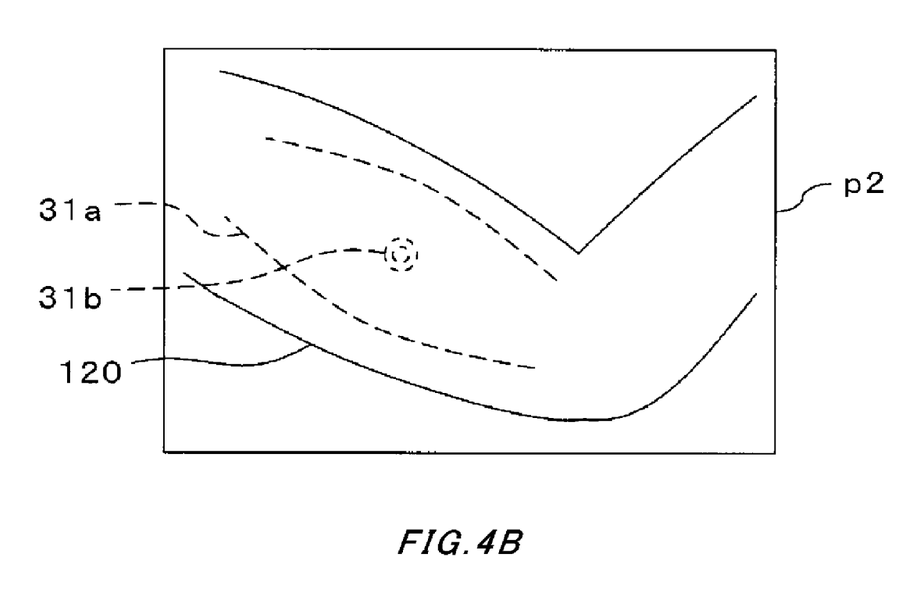
FIG. 4B is an explanatory diagram showing images processed by the positional information processing apparatus 10, showing a muscle position display map image p2 in which marks 31a indicating the position of the muscle 110 and a mark 31b indicating the position of a neuromuscular junction 112a are superposed and displayed on the body surface 120 on the basis of relative positions of the muscle 110 and the neuromuscular junction 112a to the body surface 120, detected by a muscle position detection unit 3.
Figure 4C:
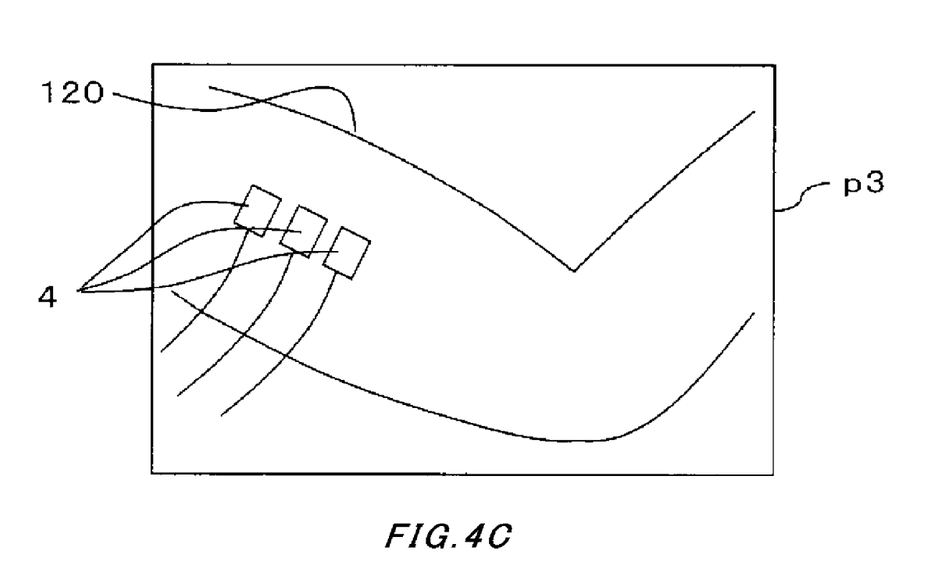
FIG. 4C is an explanatory diagram showing images processed by the positional information processing apparatus 10, showing a moving image p3 in which biomedical electrodes 4 to be brought close to the body surface 120 are captured.

As shown in FIG. 2, the positional information processing apparatus 10 includes a muscle position detection unit 3, an image recognition unit 7, an image storage unit 8, and an image composition unit 9. The potentials detected from all the myoelectric detection electrodes 21(m, n) are input to the muscle position detection unit 3 from the logger 15 each time a certain time elapses. A still image p1 shown in FIG. 4A is input to the image recognition unit 7 from the camera 16. The image storage unit 8 temporarily stores a muscle position display map image p2 shown in FIG. 4B, which is input from the muscle position detection unit 3. The image composition unit 9 outputs a composite moving image p4 shown in FIG. 4D to the display device 17. The composite moving image p4 is obtained by combining the moving image p3 shown in FIG. 4C, input from the camera 16, with the muscle position display map image p2 shown in FIG. 4B, read from the image storage unit 8.

Figure 3:
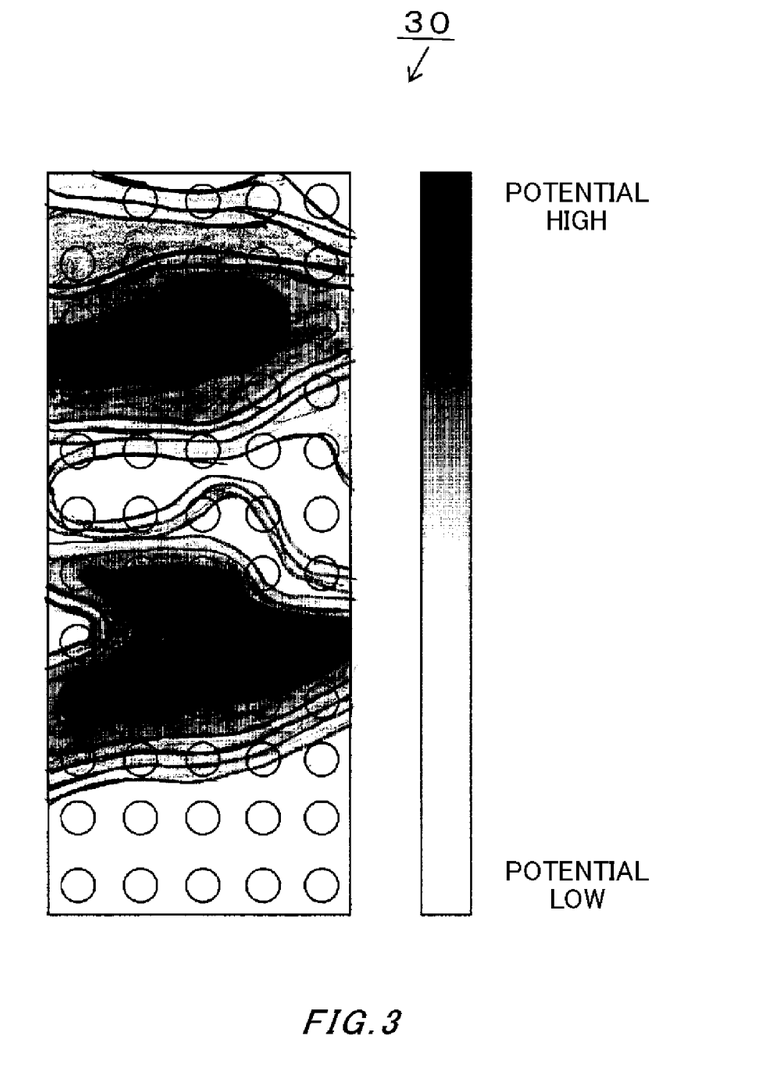
FIG. 3 shows a myoelectric potential distribution map 30 which a muscle position detection unit 3 generates from potentials detected by all myoelectric detection electrodes 21(m, n).

Each time the potentials detected by all the myoelectric detection electrodes 21(m, n) are input from the logger 15, the muscle position detection unit 3 of the positional information processing apparatus 10 virtually generates a myoelectric potential distribution map 30 such as shown in FIG. 3. The myoelectric potential distribution map 30 shows a relationship between the close contact positions of all the myoelectric detection electrodes 21(m, n) and the potentials detected by the myoelectric detection electrodes 21(m, n) at the close contact positions.

If the brachial muscle 110 makes a voluntary movement, muscle action potentials are detected from myoelectric detection electrodes 21(m, n) that are in close contact with the living body surface 120 of the brachial muscle 110. More specifically, the myoelectric detection electrodes 21(m, n) in close contact with the living body surface 120 of the brachial muscle 110 detect muscle action potentials having levels corresponding to the distances from the brachial muscle 110 to the close contact positions of the myoelectric detection electrodes 21(m, n). No muscle action potential is detected from myoelectric detection electrodes 21(m, n) that are in close contact with positions of the living body surface 120 off the brachial muscle 110. While the brachial muscle 110 makes a voluntary movement, the muscle position detection unit 3 can thus detect the relative position of the brachial muscle 110 to the position where the electrode sheet 20 is adhered to the living body surface 120 on the basis of the myoelectric potential distribution map 30 virtually generated from the potentials detected by all the myoelectric detection electrodes 21(m, n).

As the brachial muscle 110 makes a voluntary movement, a muscle action potential occurring at a neuromuscular junction 112a propagates along muscle fibers 110a of the brachial muscle 110. The muscle action potential is therefore successively detected by myoelectric detection electrodes 21(m, n) that are in close contact with different positions of the living body surface 120 along the muscle fibers 110a along which the muscle action potential propagates. While the brachial muscle 110 makes a voluntary movement, the muscle position detection unit 3 compares the potentials detected by all the myoelectric detection electrodes 21(m, n), input from the logger 15 each time a certain time elapses, and virtually generates the myoelectric potential distribution map 30. From a change of the myoelectric potential distribution map 30, the muscle position detection unit 3 can detect a relative position of the neuromuscular junction 112a to the position where the electrode sheet 20 is adhered to the living body surface 120, and a running direction of the muscle fibers 110a of the brachial muscle 110.

The camera 16 operates in a still image mode in which to capture a still image, and a moving image mode in which to capture a moving image. In the still image mode, the camera 16 outputs the still image p1, in which the electrode sheet 20 is captured in close contact with the living body surface 120 of the brachial muscle 110, to the image recognition unit 7 of the positional information processing apparatus 10. The image recognition unit 7 extracts the outline of the living body surface 120 of the brachial muscle 110 and feature portions expressing a relationship of the adhering position of the electrode sheet 20 to the living body surface 120 from the input still image p1. The image recognition unit 7 outputs the outline and the feature portions to the muscle position detection unit 3.

As described above, the muscle position detection unit 3 can detect the relative positions of the brachial muscle 110 and the neuromuscular junction 112a to the electrode sheet 20 adhered to the living body surface 120 and the running direction of the muscle fibers 110a of the brachial muscle 110 from the myoelectric potential distribution map 30. On the basis of the feature portions indicating the position of the electrode sheet 20 with respect to the living body surface 120, input from the image recognition unit 7, the muscle position detection unit 3 can thus detect the relative positions of the brachial muscle 110 and the neuromuscular junction 112a to the living body surface 120 and the running direction of the muscle fibers 110a of the brachial muscle 110 via the common electrode sheet 20. The muscle position detection unit 3 uses the detected relative position information to generate the muscle position display map image p2. In the muscle position display map image p2, marks 31a indicating the outline and the running direction (longitudinal direction) of the brachial muscle 110 and a mark 31b indicating the position of the neuromuscular junction 112a are added within the outline of the living body surface 120 of the brachial muscle 110, input from the image recognition unit 7. The muscle position detection unit 3 outputs the muscle position display map image p2 to the image storage unit 8.

The muscle position display map image p2 in which the marks 31a and 31b are displayed within the outline of the living body surface 120 of the brachial muscle 110 is relative position information indicating the relative positions of the brachial muscle 110 and the neuromuscular junction 112a to the living body surface 120. The image storage unit 8 stores the muscle position display map image p2 as brachial muscle relative position information.

If the electrode sheet 20 is moved to a living body surface 120 under which another voluntary muscle 110 lies, a muscle position display map image p2 indicating the relative position of the voluntary muscle 110 to the living body surface 120 is obtained in a similar manner. The image storage unit 8 can thus store relative position information about various types of voluntary muscles 110. After relative position information about a desired voluntary muscle 110 is stored into the image storage unit 8, the electrode sheet 20 and the positional information processing unit 10 may be disconnected.

To bring biomedical electrodes 4 into close contact with the living body surface 120 of the muscle 110 about which the relative position information is stored, the camera 16 is switched to the moving image mode. The camera 16 captures a moving image of the biomedical electrodes 4 to be brought close to the living body surface 120. For example, suppose that three biomedical electrodes 4, 4, 4 serving as a pair of stimulating electrodes and a ground electrode are brought into close contact with the living body surface 120 for the purpose of applying an electrical stimulation signal to the brachial muscle 110 for muscle training, while the position of the brachial muscle 110 is checked. The camera 16 operating in the moving image mode captures the moving image p3 shown in FIG. 4C, of a state in which the biomedical electrodes 4 are brought close to the living body surface 120 of the brachial muscle 110. The moving image p3 is output to the image composition unit 9 of the positional information processing apparatus 10.

Figure 4D:
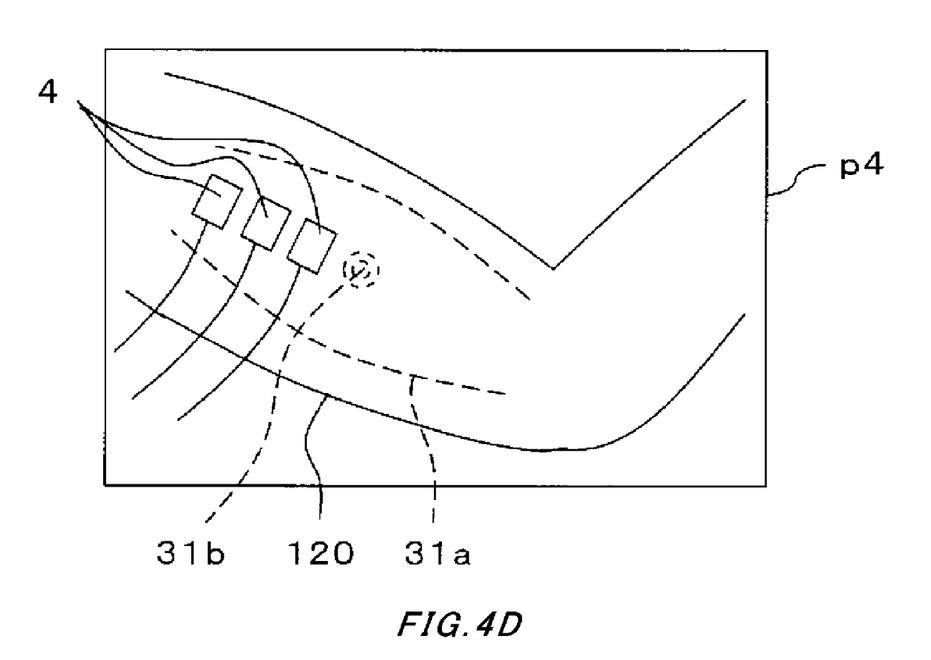
FIG. 4D is an explanatory diagram showing images processed by the positional information processing apparatus 10, showing a moving image p4 obtained by combining the still image p2 with the moving image p3 so that the outlines of the body surface 120 coincide.

While the captured moving image p3 of the living body surface 120 of the brachial muscle 110 is input from the camera 16, the image composition unit 9 reads the muscle position display map image p2 of the same brachial muscle 110. The muscle position display map image p2 is the brachial muscle relative position information stored in the image storage unit 8. The image composition unit 9 extracts common features of the living body surface 120 (for example, the outlines of the living body surface 120) in the moving image p3 and the muscle position display map image p2. The image composition unit 9 superposes the muscle position display map image p2 on the moving image p3 so that the extracted feature portion images coincide, whereby the composite moving image p4 shown in FIG. 4D is generated.

The composite moving image p4 generated by the image composition unit 9 is output to the display device 17 and continuously displayed on a display of the display device 17. As shown in FIG. 4D, the composite moving image p4 displays the marks 31a indicating the outline and the longitudinal direction of the brachial muscle 110, the mark 31b indicating the position of the neuromuscular junction 112a in the living body surface 120, and the biomedical electros 4 brought close to the living body surface 120. The operator can thus guide the biomedical electrodes 4 into close contact with optimum positions on the living body surface 120 of the brachial muscle 110 while checking the current positions of the biomedical electrodes 4 with respect to the brachial muscle 110 and the neuromuscular junction 112 on the composite moving image p4.

For example, suppose, as in the present embodiment, that the three biomedical electrodes 4, 4, 4 serving as a pair of stimulating electrodes and a ground electrode are brought into close contact with the living body surface 120 for the purpose of muscle training of the brachial muscle 110. In such a case, a stimulating electrode serving as a positive electrode, a stimulating electrode serving as a negative electrode, and the ground electrode are brought into close contact with three positions on the living body surface 120 one by one along the longitudinal direction of the outline of the brachial muscle 110 displayed on the display device 17.

Suppose that the composition, the degree of fatigue, and the like of the muscle 110 are detected from the level of the muscle action potential occurring in the muscle 110 or the propagation velocity MFCV of the muscle action potential. In such a case, a plurality of biomedical electrodes 4 for detecting the muscle action potential are brought into close contact with different positions on the living body surface 120 on one side of the neuromuscular junction 112a in the longitudinal direction of the brachial muscle 110, on the basis of the outline of the brachial muscle 110 and the position of the neuromuscular junction 112a displayed on the display device 17.

Various units of the foregoing positional information processing apparatus 10 can be constituted by executing application software installed on a portable information device such as a mobile phone. The positional information processing apparatus 10, the camera 16, and the display device 17 may be integrally configured as a camera-equipped smartphone.

In the foregoing embodiment, the relative position information indicating the relative positions of the voluntary muscle 110 and the neuromuscular junction 112a to the living body surface 120 is stored as the muscle position display map image p2 in the image storage unit 8. However, the relative positions of the voluntary muscle 110 and the neuromuscular 112a may be expressed, for example, by position coordinates with the origin at a specific position of the living body surface 120 as long as the relative positions can be identified.

In the foregoing embodiment, the moving image p4 generated by combining the muscle position display map image p2 with the captured moving image p3 of the biomedical electrodes 4 is displayed on the display device 17, and the biomedical electrodes 4 are guided to the close contact positions. However, for example, the positions of the voluntary muscle 110 and the neuromuscular junction 112a may be projected on the living body surface 120 on the basis of the relative position information indicating the relative positions of the voluntary muscle 110 and the neuromuscular junction 112a. Distances between the positions of the voluntary muscle 110 and neuromuscular junction 112a and the biomedical electrodes 4 may be notified to the user by sound or numerical indications so that the biomedical electrodes 4 are guided into optimum close contact positions.

The muscle position detection unit 3 detects the relative positions of the voluntary muscle 110 and the neuromuscular junction 112a to the living body surface 120 and the running direction of the muscle fibers 110a. However, part of the positions and direction may be detected and stored as the relative position information.

The myoelectric detection electrodes $21(m, n)$ for detecting the relative positions of the voluntary muscle 110 and the neuromuscular junction 112a are arranged in respective positions of the matrix configuration. However, the myoelectric detection electrodes $21(m, n)$ may be arranged in arbitrary positions as long as a plurality of myoelectric detection electrodes are in close contact with distributed positions of the living body surface 120 and the relative positions of the respective close contact positions to the living body surface 120 can be identified.

The embodiment of the present invention is suitable for a muscle training system in which biomedical electrodes are brought into close contact with a living body surface of a muscle for the purpose of applying an electrical stimulus to the muscle.

The embodiment of the present invention have been described with reference to block diagrams whose blocks may represent units of apparatuses responsible for performing operations. Certain units may be implemented by dedicated circuitry, programmable circuitry supplied with computer-readable instructions stored on computer-readable media, and/or processors supplied with computer-readable instructions stored on computer-readable media. Dedicated circuitry may include digital and/or analog hardware circuits and may include integrated circuits (IC) and/or discrete circuits. Programmable circuitry may include reconfigurable hardware circuits comprising logical AND, OR, XOR, NAND, NOR, and other logical operations, flip-flops, registers, memory elements, etc., such as field-programmable gate arrays (FPGA), programmable logic arrays (PLA), etc.

Computer-readable media may include any tangible device that can store instructions for execution by a suitable device, such that the computer-readable medium having instructions stored therein comprises an article of manufacture including instructions which can be executed to create means for performing operations specified in the block diagrams. Examples of computer-readable media may include an electronic storage medium, a magnetic storage medium, an optical storage medium, an electromagnetic storage medium, a semiconductor storage medium, etc. More specific examples of computer-readable media may include a floppy disk, a diskette, a hard disk, a random access memory (RAM), a read-only memory (ROM), an erasable programmable read-only memory (EPROM or Flash memory), an electrically erasable programmable read-only memory (EEPROM), a static random access memory (SRAM), a compact disc read-only memory (CD-ROM), a digital versatile disk (DVD), a BLU-RAY® disc, a memory stick, an integrated circuit card, etc.

Computer-readable instructions may include assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, JAVA, C++, etc., and conventional procedural programming languages, such as the "C" programming language or similar programming languages.

Computer-readable instructions may be provided to a processor of a general purpose computer, special purpose computer, or other programmable data processing apparatus, or to programmable circuitry, locally or via a local area network (LAN), wide area network (WAN) such as the Internet, etc., to execute the computer-readable instructions to create means for performing operations specified in the block diagrams. Examples of processors include computer processors, processing units, microprocessors, digital signal processors, controllers, microcontrollers, etc.

REFERENCE SIGNS LIST 1 apparatus for guiding biomedical electrode
3 muscle position detection unit (muscle position detecting unit)
4 biomedical electrode
8 image storage unit (storing unit)
10 positional information processing apparatus (guiding unit)
16 camera (guiding unit)
17 display device (guiding unit)
31a mark indicating position of muscle (marker)
31b mark indicating position of neuromuscular junction
110 voluntary muscle
110a muscle fiber
112a neuromuscular junction

The invention claimed is:

1. An apparatus for guiding a biomedical electrode comprising:
a plurality of myoelectric detection electrodes configured to make close contact with respective positions on a living body surface and each detect a muscle action potential occurring when a voluntary muscle inside the living body surface expands and contracts, the positions being distributed over a two-dimensional plane;
a muscle position detecting unit for detecting a relative position of the voluntary muscle and/or a neuromuscular junction of the voluntary muscle to the living body surface from a myoelectric potential distribution of the muscle action potentials detected by the respective myoelectric detection electrodes over the two-dimensional plane and/or from a temporal change of the myoelectric potential distribution;
a storing unit for storing relative position information about the voluntary muscle and/or the neuromuscular junction of the voluntary muscle to the living body surface; and
a guiding unit for guiding a close contact position of a biomedical electrode to be brought into close contact with the living body surface of the voluntary muscle on a basis of the detected relative position information;
wherein the relative position information is a muscle position display map image in which the voluntary muscle and/or the neuromuscular junction of the voluntary muscle of which the relative position(s) is/are detected by the muscle position detecting unit is/are superposed and displayed on an image showing the living body surface,
wherein the guiding unit includes:
a camera configured to capture a moving image of a state in which the biomedical electrode is brought close to the living body surface of the voluntary muscle;
an image composition unit for combining the muscle position display map image with the moving image to generate a composite moving image so that feature portion images of the living body surface included in the muscle position display map image and the moving image in common coincide; and
a display device that displays the composite moving image.

2. The apparatus for guiding a biomedical electrode according to claim 1, wherein the guiding unit displays a marker indicating the voluntary muscle and/or the neuromuscular junction of the voluntary muscle on the living body surface of the voluntary muscle for the biomedical electrode to be brought close to on a basis of the relative position information.

3. The apparatus for guiding a biomedical electrode according to claim 1, wherein the guiding unit expresses, by sound or display, a distance between the voluntary muscle and/or the neuromuscular junction of the voluntary muscle and the biomedical electrode to be brought close to the living body surface of the voluntary muscle on a basis of the relative position information.

4. The apparatus for guiding a biomedical electrode according to claim 1, wherein
the muscle position detecting unit detects the relative position of the voluntary muscle to the living body surface, and
the guiding unit is adapted to guide at least a pair of the plurality of myoelectric detection electrodes to different close contact positions on the living body surface along a longitudinal direction of the voluntary muscle, the at least the pair of the plurality of myoelectric detection electrodes each detecting a muscle action potential occurring from the voluntary muscle.

5. The apparatus for guiding a biomedical electrode according to claim 1, wherein
the muscle position detecting unit detects the relative position of the neuromuscular junction of the voluntary muscle to the living body surface, and
the guiding unit is adapted to guide at least a pair of the plurality of myoelectric detection electrodes to different close contact positions on the living body surface on one side of the neuromuscular junction of the voluntary muscle in a longitudinal direction of the voluntary muscle, the at least the pair of the plurality of myoelectric detection electrodes each detecting a muscle action potential occurring from the voluntary muscle.

* * * * *